(12) United States Patent
Maeda et al.

(10) Patent No.: US 10,605,671 B2
(45) Date of Patent: Mar. 31, 2020

(54) CHROMATOGRAPH DATA PROCESSING DEVICE, CHROMATOGRAPH DATABASE, CHROMATOGRAPH DATA PROCESSING METHOD, AND PROGRAM FOR CHROMATOGRAPH DATA PROCESSING DEVICE

(71) Applicant: HORIBA STEC, CO., LTD., Kyoto (JP)

(72) Inventors: Tsuneaki Maeda, Kyoto (JP); Nanako Sasaki, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 1162 days.

(21) Appl. No.: 14/894,105

(22) PCT Filed: Dec. 9, 2014

(86) PCT No.: PCT/JP2014/082519
§ 371 (c)(1),
(2) Date: Nov. 25, 2015

(87) PCT Pub. No.: WO2015/087864
PCT Pub. Date: Jun. 18, 2015

(65) Prior Publication Data
US 2016/0103021 A1 Apr. 14, 2016

(30) Foreign Application Priority Data
Dec. 9, 2013 (JP) .................................. 2013-254444

(51) Int. Cl.
*G01K 3/00* (2006.01)
*G01N 30/86* (2006.01)
(Continued)

(52) U.S. Cl.
CPC ........... *G01K 3/00* (2013.01); *G01N 30/8675* (2013.01); *G01N 30/88* (2013.01); *G01N 30/54* (2013.01)

(58) Field of Classification Search
CPC ...... G01K 3/00; G01N 30/88; G01N 30/8675; G01N 30/54
See application file for complete search history.

(56) References Cited

U.S. PATENT DOCUMENTS 5,958,246 A * 9/1999 Tipler .................... G01N 30/62
210/656
6,691,053 B2 * 2/2004 Quimby ............. G01N 30/8665
435/6.12

(Continued)

FOREIGN PATENT DOCUMENTS

WO 2012/118209 9/2012

OTHER PUBLICATIONS

Akporhonor et al., "Calculation of programmed temperature gas chromatographic characteristics from isothermal data", Journal of Chromatography, 1990, pp. 269-278, 04, vol. 504, No. 2.

(Continued)

*Primary Examiner* — Stephanie E Bloss
(74) *Attorney, Agent, or Firm* — Grennblum & Bernstein, P.L.C.

(57) ABSTRACT

To provide a chromatograph data processing device and the like that can estimate and calculate a retention index or a retention time that would be measured by performing programmed-temperature analysis with any desired rate of temperature increase from known retention indices measured by programmed-temperature analysis, a receiving unit that receives a rate of temperature increase, an RI-r relationship storage unit that stores an RI-r relationship, the RI-r relationship being a relationship between a retention index and a rate of temperature increase and being identified based (Continued)

on a plurality of retention indices with respect to different rates of temperature increase and the corresponding rates of temperature increase, and a retention index calculation unit that calculates an estimated retention index based on the RI-r relationship, the estimated retention index being a retention index corresponding to the received rate of temperature increase received by the receiving unit.

11 Claims, 7 Drawing Sheets

(51) Int. Cl.
  *G01N 30/88* (2006.01)
  *G01N 30/54* (2006.01)

(56) References Cited

U.S. PATENT DOCUMENTS

| | | | | |
|---|---|---|---|---|
| 9,222,923 | B2* | 12/2015 | Sasaki | G01N 30/8675 |
| 2014/0067304 | A1* | 3/2014 | Sasaki | G01N 30/8658 |
| | | | | 702/89 |
| 2014/0188403 | A1* | 7/2014 | Sasaki | G01N 30/8675 |
| | | | | 702/24 |
| 2014/0309946 | A1* | 10/2014 | Kono | G01N 30/8675 |
| | | | | 702/24 |

OTHER PUBLICATIONS

Manral et al., "Gas Chromatographic Retention Indices of Fentanyl and Analogues", Journal of Chromatographic Science, 2008, pp. 551-555, vol. 46.

International Search Report issued in PCT/JP2014/082519, dated Mar. 17, 2015.

S. E. Stein, "Gas Chromatograhy", in NIST Chemistry WebBook, NIST Standard Reference Database No. 69, Eds. P.J.Linstrom and W.G. Mallard, National Institute of Standards and Technology, Gaitherburg, MD, 20899, USA, retrieved on Sep. 18, 2018, Jun. 2005.

Office Action issued in Japan Counterpart Patent Appl. No. 2015-552452, dated Aug. 9, 2018, along with an English translation thereof.

* cited by examiner

CHROMATOGRAPH DATA PROCESSING DEVICE, CHROMATOGRAPH DATABASE, CHROMATOGRAPH DATA PROCESSING METHOD, AND PROGRAM FOR CHROMATOGRAPH DATA PROCESSING DEVICE

TECHNICAL FIELD

The present invention relates to a chromatograph data processing device and the like for converting a value measured by chromatographic analysis under certain measurement conditions into a value that would be measured under other measurement conditions.

BACKGROUND ART

Examples of analysis methods that use a gas chromatograph include isothermal analysis in which the temperature in the column is kept constant and programmed-temperature analysis in which the temperature in the column is increased at a constant rate of temperature increase. Even with respect to the same sample, retention index values measured by these analysis methods are different if the set temperatures or rates of temperature increase are different. For this reason, conventionally, in qualitative analysis of an unknown specimen, the retention index of the unknown specimen is measured under the same temperature conditions as those used in measurement of a known retention index, and a comparison is performed.

Thus, in order to enable comparison between retention indices without the necessity for setting the same temperature conditions, the applicant of the present invention proposes, as disclosed in Patent Document 1, a method for estimating a retention index of a specific sample that would be obtained by performing isothermal analysis at any desired temperature from a plurality of retention indices that have been measured with respect to that sample by performing isothermal analysis at different temperatures, and a method for estimating a retention index that would be obtained by performing programmed-temperature analysis with any desired rate of temperature increase and initial temperature from a plurality of retention indices that have been measured by performing isothermal analysis at different temperatures.

Incidentally, in actual gas chromatographic analysis, programmed-temperature analysis, which can provide measurement results within a shorter period of time than isothermal analysis, is often used. Accordingly, there is a demand for an approach that can effectively use data on retention indices that have been previously measured by programmed-temperature analysis and accumulated, rather than a method for estimating a retention index based on retention indices measured by isothermal analysis.

However, a method for estimating, from known retention indices measured by programmed-temperature analysis, a retention index that would be measured with another rate of temperature increase is currently not known.

CITATION LIST

Patent Documents

Patent Document 1: WO 2012/118209

SUMMARY OF INVENTION

Technical Problem

The present invention was made in view of problems such as those described above, and it is an object thereof to provide a gas chromatograph data processing device and the like that can estimate and calculate, from known retention indices measured by programmed-temperature analysis, a retention index or a retention time that would be measured by performing programmed-temperature analysis with any desired rate of temperature increase.

Solution to Problem

That is to say, the present invention was made for the first time by the inventor of the present application finding as a result of in-depth research that there is a one-to-one correspondence between a retention index that is measured by a programmed-temperature analysis and a rate of temperature increase that is set in measurement of this retention index, and that a retention index that would be measured by a programmed-temperature analysis in which any desired rate of temperature increase is set can be estimated using this relationship.

More specifically, a chromatograph data processing device according to the present invention includes a receiving unit that receives a rate of temperature increase, an RI-r relationship storage unit that stores an RI-r relationship, the RI-r relationship being a relationship between a retention index and a rate of temperature increase and being identified (determined) based on a plurality of retention indices with respect to different rates of temperature increase and the corresponding rates of temperature increase, and a retention index calculation unit that calculates an estimated retention index based on the RI-r relationship, the estimated retention index being a retention index corresponding to a received rate of temperature increase that is the rate of temperature increase received by the receiving unit.

Here, the RI-r relationship is a concept that covers a relation itself indicating the relationship between the retention index and the rate of temperature increase or coefficients and the like of a polynomial constituting that relation.

Thus, it is possible to create the RI-r relationship in advance from a plurality of retention indices with respect to different rates of temperature increase and calculate an estimated retention index corresponding to a received rate of temperature increase based on this RI-r relationship. Accordingly, in the case where, for example, an unknown specimen is to be qualitatively analyzed by programmed-temperature analysis, it is no longer necessary to set the rate of temperature increase for that unknown specimen to be the same as those of pervious measurement examples, and the qualitative analysis can be performed by inputting a rate of temperature increase that is set for the qualitative analysis of that unknown specimen to the receiving unit, allowing the retention index calculation unit to calculate estimated retention indices of respective substances with respect to the received rate of temperature increase, and thereby comparing the retention indices.

Moreover, a retention index corresponding to a rate of temperature increase with respect to which no actual measurement has been performed can be estimated without using retention indices measured by isothermal analysis but using only retention indices measured by programmed-temperature analysis. Thus, it is possible to effectively use data on retention indices previously measured by programmed-temperature analysis.

In order to estimate an estimated retention index by associating the rate of temperature increase with the retention index via a variable, that is, the retention temperature and increase the estimation accuracy even more, a configuration is conceivable in which the RI-r relationship from retention indices measured by programmed-temperature analysis is constituted by an HT-r relationship that is a relationship between the retention temperature and the rate of temperature increase and that is identified based on a plurality of retention indices with respect to different rates of temperature increase and the corresponding rates of temperature increase and an RI-HT relationship that is a relationship between the retention index and the retention temperature and that is identified based on a plurality of retention indices with respect to different rates of temperature increase and the corresponding rates of temperature increase, the RI-r relationship storage unit includes an HT-r relationship storage unit that stores the HT-r relationship and an RI-HT relationship storage unit that stores the RI-HT relationship, and the retention index calculation unit includes a retention temperature calculation unit that calculates an estimated retention temperature based on the HT-r relationship, the estimated retention temperature being a retention temperature corresponding to the received rate of temperature increase, and an estimated result calculation unit that calculates, based on the RI-HT relationship, a retention index corresponding to the estimated retention temperature as the estimated retention index.

Since the relationship between the retention index and the rate of temperature increase is divided into the two relationships, that is, the relationship between the retention temperature and the rate of temperature increase and the relationship between the retention index and the retention temperature as described above, even in the case where the relationship between the retention index and the rate of temperature increase has nonlinearity and thus cannot be accurately identified without a large number of data items, the relationship can be accurately identified.

In order that the relationship between the retention temperature and the rate of temperature increase can be represented by a linear equation and the HT-r relationship derived if only at least two retention indices with respect to different rates of temperature increase are present, it is sufficient if the HT-r relationship is represented by a relation in which an inverse of the retention temperature and a logarithm of the rate of temperature increase are variables.

In order that the relationship between the retention index and the retention temperature can be accurately derived using at least two retention indices with respect to different rates of temperature increase, it is sufficient if the RI-HT relationship is represented by a relation in which the retention index and the inverse of the retention temperature are variables.

In order that no matter what rate of temperature increase is received by the receiving unit, an estimated retention index corresponding to the received rate of temperature increase can be appropriately estimated and calculated from known retention indices measured by programmed-temperature analysis, it is sufficient if the chromatograph data processing device further includes an HT-r relationship identification unit that identifies the HT-r relationship based on a plurality of rates of temperature increase and retention temperatures corresponding to the respective rates of temperature increase and an RI-HT relationship identification unit that identifies the RI-HT relationship based on a plurality of retention indices and retention temperatures corresponding to the respective retention indices, wherein the HT-r relationship storage unit is configured to store the HT-r relationship identified by the HT-r relationship identification unit, and the RI-HT relationship storage unit is configured to store the RI-HT relationship identified by the RI-HT relationship identification unit.

For example, in order that an estimated retention index corresponding to any desired received rate of temperature increase can be estimated and calculated without the necessity for calculation of a retention temperature if only a pair of rates of temperature increase and corresponding retention indices are present, it is sufficient if the RI-r relationship is represented by a relation in which the retention index and the logarithm of the rate of temperature increase are variables.

A specific configuration example for making it possible to estimate and calculate on an as-needed basis an estimated retention index corresponding to any desired received rate of temperature increase without the necessity for calculation of a retention temperature is the chromatograph data processing device further including an RI-r relationship identification unit that identifies the RI-r relationship based on a plurality of retention indices and rates of temperature increase corresponding to the respective retention indices, wherein the RI-r relationship storage unit is configured to store the RI-r relationship identified by the RI-r relationship identification unit.

In order that a retention time actually measured by qualitative analysis or the like of an unknown specimen can be directly compared without being converted into a retention index, it is sufficient if the chromatograph data processing device further includes an estimated retention time calculation unit that calculates an estimated retention time that is a retention time corresponding to the estimated retention index.

An example of a data processing method for making it possible to estimate a retention index with respect to any desired rate of temperature increase from known retention indices measured by programmed-temperature analysis is a chromatograph data processing method including a receiving step of receiving a received rate of temperature increase, an RI-r relationship storing step of storing an RI-r relationship that is a relationship between a retention index and a rate of temperature increase, and a retention index calculating step of calculating an estimated retention index based on the RI-r relationship, the estimated retention index being a retention index corresponding to the received rate of temperature increase.

In order to add the function of enabling estimation of a retention index with respect to any desired rate of temperature increase from known retention indices measured by programmed-temperature analysis to an existing chromatograph data processing device, it is sufficient if a program for a chromatograph data processing device is used, the program causing a computer to perform the functions of a receiving unit that receives a received rate of temperature increase, an RI-r relationship storage unit that stores an RI-r relationship, the RI-r relationship being a relationship between a retention index and a rate of temperature increase, and a retention index calculation unit that calculates an estimated retention index based on the RI-r relationship, the estimated retention index being a retention index corresponding to the received rate of temperature increase. It should be noted that this program may be electronically distributed or may be recorded in a recording medium such as a CD, a DVD, a flash memory, or the like.

In order that a retention index with respect to any desired rate of temperature increase can be estimated and calculated in a short period of time using the RI-r relationship that is prepared in advance, it is sufficient if a chromatograph database is used, the chromatograph database including an RI-r relationship storage unit that stores an RI-r relationship with respect to each of a plurality of substances, the RI-r relationship being a relationship between a retention index and a rate of temperature increase.

Advantageous Effects of Invention

As described above, according to the chromatograph data processing device of the present invention, it is possible to calculate an estimated retention index corresponding to any desired received rate of temperature increase based on the RI-r relationship that was found by the inventor of the present application, the RI-r relationship being identified from known retention indices measured by programmed-temperature analysis. That is to say, if only a plurality of known retention indices and corresponding rates of temperature increase are known, a retention index with respect to any desired rate of temperature increase can be estimated. Thus, in qualitative analysis and the like of an unknown specimen, it is no longer necessary to set the same rate of temperature increase as that of a previously performed measurement.

LIST OF REFERENCE NUMERALS

100 Gas chromatograph data processing device
1 Known RI data storage unit
2 RI-r relationship identification unit
21 HT-r relationship identification unit
22 RI-HT relationship identification unit
3 RI-r relationship storage unit
31 HT-r relationship storage unit
32 RI-HT relationship storage unit
4 Receiving unit
5 Retention index calculation unit
51 Retention temperature calculation unit
52 Estimated result calculation unit
6 Retention time calculation unit

DESCRIPTION OF EMBODIMENTS

A gas chromatograph data processing device 100 according to a first embodiment of the present invention will be described with reference to FIGS. 1 to 3.

The gas chromatograph data processing device 100 is a device for estimating and calculating a retention index (RI) and a retention time (RT) of a specific sample with respect to any desired rate of temperature increase (r), based on a plurality of retention indices that have been measured with respect to the specific sample by programmed-temperature analyses in which different rates of temperature increase are set as well as the corresponding rates of temperature increase. It should be noted that the first embodiment assumes that in the programmed-temperature analyses, the same initial temperature is used, the temperature is increased from the point in time when the sample is injected into the column, and there is no time period in which the temperature is kept constant.

Figure 1:
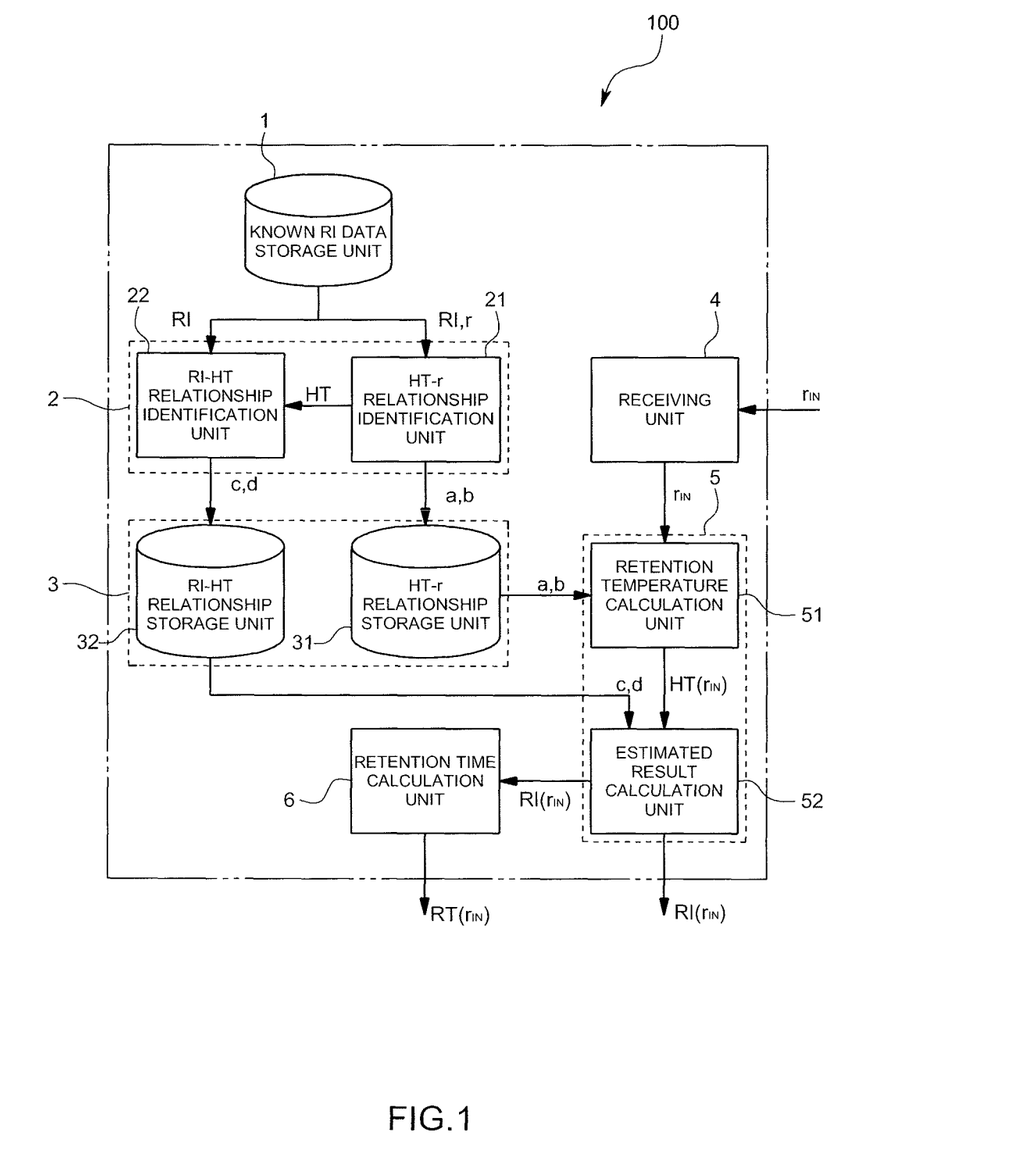
FIG. 1 shows a gas chromatograph data processing device according to a first embodiment of the present invention.
Figure 2:
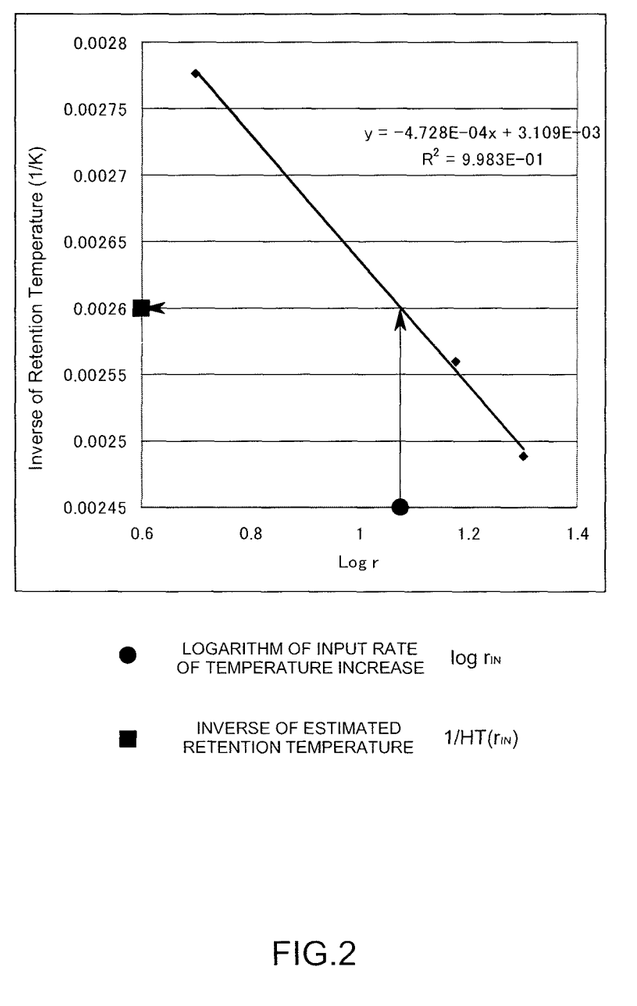
FIG. 2 is a schematic graph showing an HT-r relationship and a method for calculating an estimated retention temperature from a received rate of temperature increase according to the first embodiment.

More specifically, the functions of the gas chromatograph data processing device 100 are realized by a so-called computer that includes a CPU, a memory, an input/output means, and the like, and the gas chromatograph data processing device 100 performs at least the functions of a known RI data storage unit 1, an RI-r relationship identification unit 2, an RI-r relationship storage unit 3, a receiving unit 4, a retention index calculation unit 5, and a retention time calculation unit 6 as shown in the functional block diagram of FIG. 1 by a program for a gas chromatograph data processing device stored in the memory being executed and the various units cooperating with each other.

A detailed description of the various units is given below. First, the known RI data storage unit 1, the RI-r relationship identification unit 2, and the RI-r relationship storage unit 3 that constitute a database portion providing the basis for the retention index estimation will be described.

In the known RI data storage unit 1, for each type of samples, retention indices that have been actually measured by programmed-temperature analysis before and temperature increase conditions including the rate of temperature increase, the initial temperature, and the like that have been used during measurement of these retention indices are stored as pairs. In the first embodiment, in order to estimate a retention index with respect to a rate of temperature increase at which no measurement has been performed, actually measured data in which retention indices and corresponding rates of temperature increase are contained as pairs is used.

The RI-r relationship identification unit 2 identifies an RI-r relationship, which is a relationship between the retention index and the rate of temperature increase with respect to a specific sample. In the first embodiment, the RI-r relationship is defined by dividing it into two different relationships, and the RI-r relationship is constituted by an HT-r relationship that is a relationship between the retention temperature (it should be noted that in the following description the retention temperature may also be referred to as HT so as to be easily distinguished from the retention time) and the rate of temperature increase and that is identified based on these values and an RI-HT relationship that is a relationship between the retention index and the retention temperature and that is identified based on these values. More specifically, the RI-r relationship identification unit 2 is composed of an HT-r relationship identification unit 21 that identifies the HT-r relationship and an RI-HT relationship identification unit 22 that identifies the RI-HT relationship.

The RI-r relationship storage unit 3 stores relations that are identified by the RI-r relationship identification unit 2, and is composed of an HT-r relationship storage unit 31 that stores the HT-r relationship and an RI-HT relationship storage unit 32 that stores the RI-HT relationship.

The HT-r relationship identification unit 21 identifies, based on a plurality of data items, that is, pairs of retention temperatures and rates of temperature increase, with respect to a specific sample, an approximate equation indicating the HT-r relationship and stores coefficients of respective terms representing that approximate equation in the HT-r relationship storage unit 31.

Here, a procedure that is performed by the HT-r relationship identification unit 21 to identify the approximate equation, which indicates the HT-r relationship, will be described in detail. The HT-r relation identification unit 21 calculates retention temperatures from the plurality of data items, that is, the pairs of the retention indices and the rates of temperature increase, stored in the known RI data storage unit 1 and then identifies an approximate equation indicating the HT-r relationship.

Retention temperature is defined by Equation 1 based on the retention time, which is the amount of time from the injection of a specific sample into the column until the detection thereof, and the rate of temperature increase during programmed-temperature analysis.

Equation 1

$$T_r = rt_R + T_0 \tag{1}$$

where $T_r$ is the retention temperature, r is the rate of temperature increase, $t_R$ is the retention time, and $T_0$ is the initial temperature.

Moreover, if a retention index of a specific sample and adjusted retention times of alkanes that are measured at the same rate of temperature increase as that used when the retention index is measured are known, the adjusted retention time of the specific sample can be calculated based on Equation 2.

Equation 2

$$RI = \frac{t'(X) - t'(P_z)}{t'(P_{z+1}) - t'(P_z)} \times 100 + 100 \times Z \tag{2}$$

where RI is the retention index of a sample, t'(X) is the adjusted retention time of the sample, $t'(P_z)$ is the adjusted retention time of an alkane having Z carbon atoms, and $t'(P_{z+1})$ is the adjusted retention time of an alkane having Z+1 carbon atoms, and the adjusted retention times are the values that are measured under the same programmed-temperature analysis conditions as those used in measurement of the retention index. Moreover, since the adjusted retention time is a value obtained by subtracting the hold-up time, which is the time taken for a component that is not retained on the column, such as methane, to travel through the column, from the retention time, it is possible to calculate the retention time if the adjusted retention time is known. It should be noted that with respect to the adjusted retention times of the alkanes, known data may be used, or data that is actually measured by setting the same rate of temperature increase as that used in the measurement of the retention index of the sample may be used.

As described above, the HT-r relationship identification unit 21 calculates retention temperatures based on Equations 1 and 2 from combinations of known retention indices and rates of temperature increase. Furthermore, the HT-r relationship identification unit 21 is configured to identify an approximate equation indicating an HT-r relationship as shown in FIG. 2, as a linear equation in which the inverse of the retention temperature ($1/T_r$) and the logarithm of the rate of temperature increase (log r) are variables. Moreover, coefficients a and b of the identified approximate equation are stored in the HT-r relationship storage unit 31 for each type of samples.

Since the linearity can be obtained by setting the variables in the above-described manner, if known data containing at a minimum of two pairs of retention indices and rates of temperature increase are present, the HT-r relationship can be accurately identified even when the number of data items is small. It should be noted that the existence of a linear relationship between the inverse of the retention temperature and the logarithm of the rate of temperature increase can be derived from Equation 3 representing a relationship that holds between the migration rate and the saturated vapor pressure.

Equation 3

$$\ln P_0 = \frac{\Delta H_V}{RT} + \alpha \tag{3}$$

where $P_0$ is the saturated vapor pressure, $\Delta H_v$ is the latent heat of vaporization per mole, R is the gas constant, and T is the absolute temperature, and Equation 4 can be derived based on Equation 3.

Equation 4

$$\ln r = -\frac{A}{T_r} + B \tag{4}$$

That is to say, the existence of a linear relationship between the logarithm of the rate of temperature increase r and the inverse of the retention temperature $T_r$ can be derived based on Equation 3. Here, in Equation 4, the rate of temperature increase r and the retention temperature $T_r$ are the only variables, and therefore if the initial temperature $T_0$ and the like that are parameters other than the rate of temperature increase r, of the parameters related to the oven temperature, are different, the same result cannot be obtained. Accordingly, in the present embodiment, with respect to the data on known retention indices that are used to identify the HT-r relationship, the initial temperature $T_0$ is uniform even though the rate of temperature increase r varies. Moreover, no retention indices that are measured by performing a multistage temperature increase in which the temperature is kept at a constant temperature in the course of the temperature increase are used, and only retention indices that are measured by keeping a constant rate of temperature increase r all the time from the injection of the sample into the column until the detection thereof are used.

Next, a procedure for identifying the RI-HT relationship will be described. Based on a plurality of data items, that is, pairs of retention indices and corresponding retention temperatures that are calculated by the HT-r relationship identification unit 21, with respect to a specific sample, the RI-HT relationship identification unit 22 identifies an approximate equation indicating the RI-HT relationship, and stores coefficients of respective terms representing that approximate equation in the RI-HT relationship storage unit 32.

Figure 3:
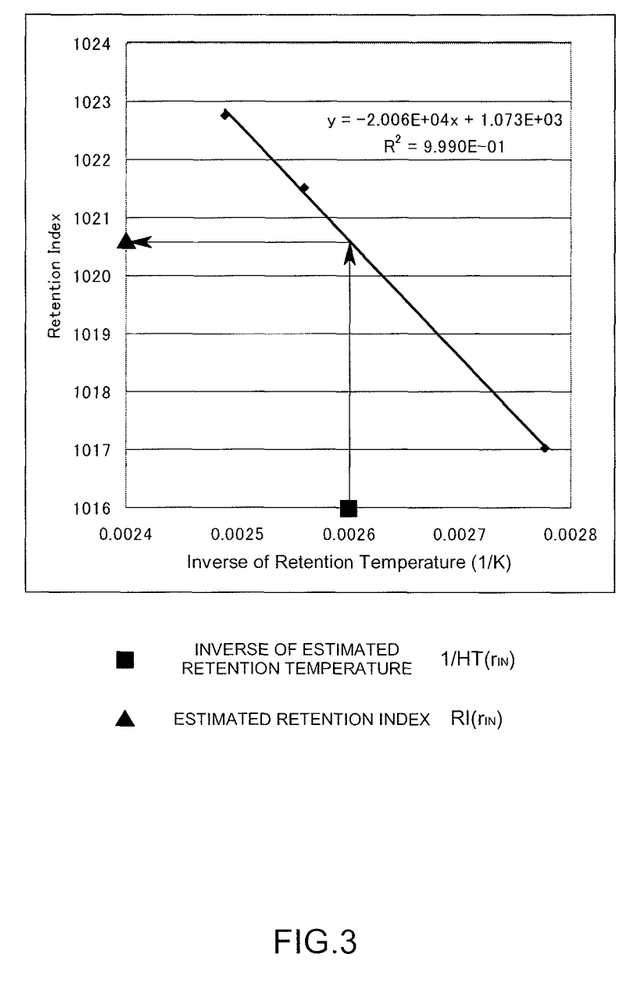
FIG. 3 is a schematic graph showing an RI-HT relationship and a method for calculating an estimated retention index from the estimated retention temperature according to the first embodiment.

More specifically, the RI-HT relationship identification unit 22 is configured to identify an approximate equation indicating the RI-HT relationship as a linear equation in which the retention index (RI) and the inverse of the retention time ($1/T_r$) are variables as shown in the graph of FIG. 3. Since it is possible to achieve the linearity in a predetermined section by setting such variables, the RI-HT relationship can be accurately identified if only at least two sets of retention indices and corresponding retention temperatures are present. Coefficients c and d of the identified approximate equation are stored in the RI-HT relationship storage unit 32 for each type of samples.

Next, the receiving unit 4, the retention index calculation unit 5, and the retention time calculation unit 6, which constitute a configuration for estimating a retention index and a retention time with respect to a rate of temperature increase at which no actual measurement has been performed, using an HT-r relationship and an RI-HT relationship that are identified based on known data will be described.

As shown in FIG. 1, the receiving unit 4 receives the type of the sample and the rate of temperature increase with respect to which a user desires to estimate a retention index, and the rate of temperature increase that is input by the user is used as a received rate of temperature increase ($r_{IN}$) in the various units. For example, a rate of temperature increase that is set by the user when performing programmed-temperature analysis using a gas chromatograph is received by the receiving unit 4 as the received rate of temperature increase.

The retention index calculation unit 5 calculates, with respect to the sample of the type that is received by the receiving unit 4, an estimated retention index ($RI(r_{IN})$) corresponding to the received rate of temperature increase based on the RI-r relationship. More specifically, the retention index calculation unit 5 is composed of a retention temperature calculation unit 51 that calculates an estimated retention temperature (HT ($r_{IN}$)) corresponding to the received rate of temperature increase based on the HT-r relationship, and an estimated result calculation unit 52 that calculates, based on the RI-HT relationship, an estimated retention index corresponding to the estimated retention temperature calculated by the retention temperature calculation unit 51.

The retention temperature calculation unit 51 calculates an estimated retention temperature corresponding to the received rate of temperature increase based on the coefficients a and b of an approximate equation indicating the HT-r relationship, the coefficients being stored in the HT-r relationship storage unit 31. For example, as shown in FIG. 2, a retention temperature value corresponding to the received rate of temperature increase on an approximate straight line is calculated as the estimated retention temperature by the retention temperature calculation unit 51.

The estimated result calculation unit 52 calculates an estimated retention index corresponding to the estimated retention temperature based on the coefficients c and d of an approximate equation indicating the RI-HT relationship, the coefficients being stored in the RI-HT relationship storage unit 32. For example, a retention index value corresponding to the estimated retention temperature on the approximate straight line in FIG. 3 is output from the estimated result calculation unit 52 as the estimated retention index.

The retention time calculation unit 6 calculates an estimated retention time ($RT(r_{IN})$) based on the estimated retention index calculated by the retention index calculation unit 5. More specifically, the estimated retention time is calculated based on Equation 1, that is, the equation that defines a retention index. Here, if adjusted retention times of alkanes that are measured with the received rate of temperature increase are not held as data, these values can be actually measured.

Next, the fact that the configurations as described above allow an estimated retention temperature and an estimated retention index to be estimated with a predetermined estimation accuracy relative to values that would be actually measured will be described based on the results of experiments.

First, it is assumed that the known RI data storage unit 1 stores data as shown in Table 1 below for each type of samples, the data containing actually measured retention indices and rates of temperature increase that are used during the measurement as pairs.

TABLE 1

| Rate of temperature increase (° C./min) | Actually measured retention index | | | |
|---|---|---|---|---|
| | 2-Octanone | 1-Octanol | 2,6-Dimethylphenol | 2,6-Dimethylaniline |
| 5 | 970.746 | 1052.17 | 1075.52 | 1128.21 |
| 10 | 969.682 | 1052.01 | 1077.95 | 1133.42 |
| 15 | 969.459 | 1051.89 | 1079.77 | 1136.89 |
| 20 | 969.559 | 1051.93 | 1081.17 | 1139.45 |

Figure 4:
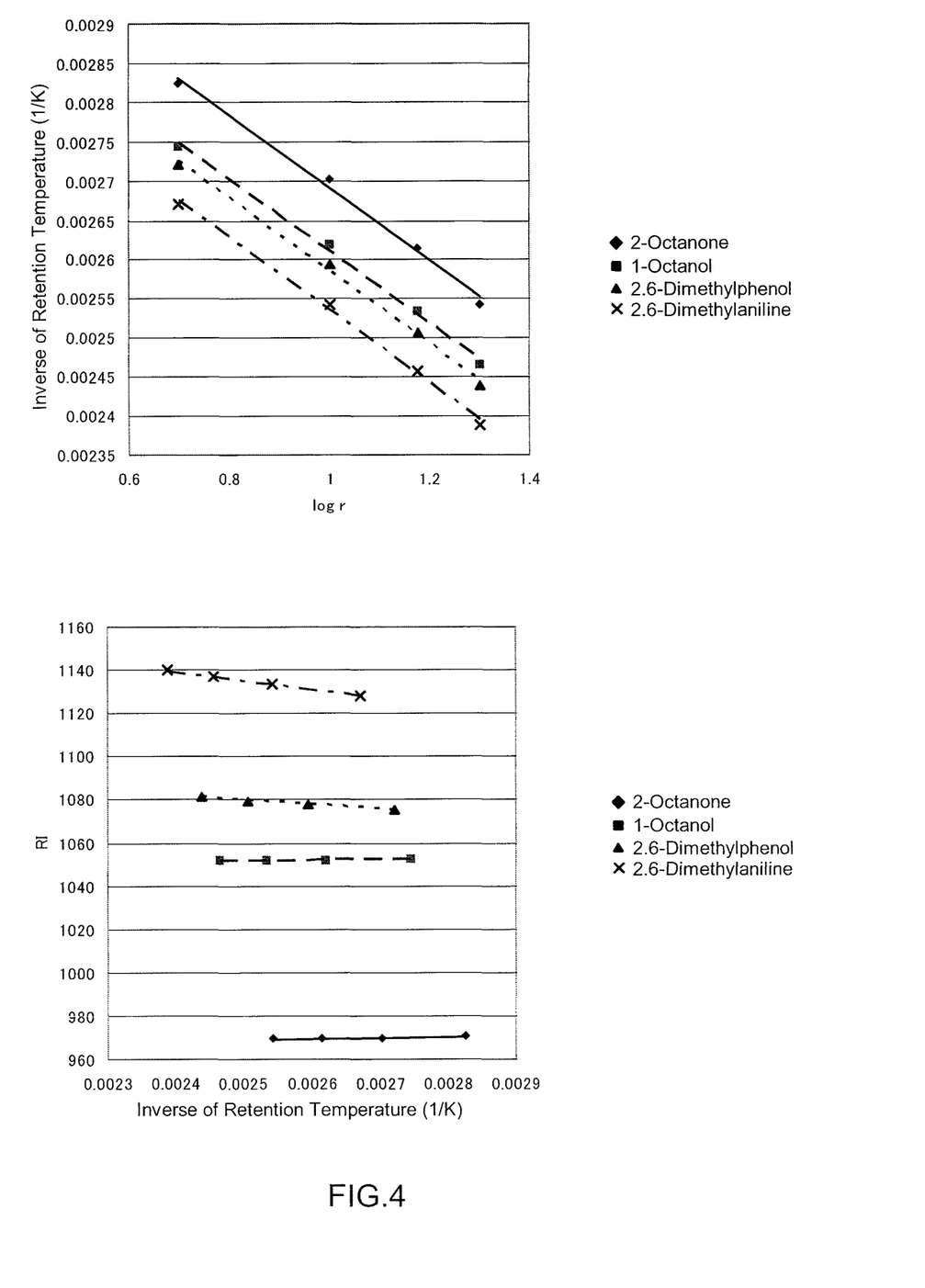
FIG. 4 shows graphs showing the results of identification of relationships based on actually measured data according to the first embodiment.

Using these known values, the HT-r relationship identification unit 21 and the RI-HT relationship identification unit 22 identify the coefficients of approximate straight lines indicating the HT-r relationships and the RI-HT relationships with respect to the individual samples as shown in FIG. 4. The coefficients a and b as well as c and d that indicate the slopes and intercepts of the approximate straight lines indicating the HT-r relationships and the RI-HT relationships with respect to the individual samples are as shown in Table 2.

TABLE 2

| | HT-r relationship | | | |
|---|---|---|---|---|
| | 2-Octanone | 1-Octanol | 2,6-Dimethylphenol | 2,6-Dimethylaniline |
| Slope a | −0.000465394 | −0.000459529 | −0.000466191 | −0.000466188 |
| Intercept b | 0.00315694 | 0.00307050 | 0.00305252 | 0.00300136 |
| | RI-HT relationship | | | |
| | 2-Octanone | 1-Octanol | 2,6-Dimethylphenol | 2,6-Dimethylaniline |
| Slope c | 4325.96 | 961.416 | −20024.8 | −39895.5 |
| Intercept d | 958.306 | 1049.51 | 1129.98 | 1234.82 |

Here, in the case where the receiving unit 4 received 8° C./min as the received rate of temperature increase, estimated retention indices of the samples that were estimated by the retention index calculation unit 5 using the values in Table 2 and actually measured retention indices of the samples that were actually measured by programmed-temperature analysis at 8° C./min, which is equal to the received rate of temperature increase, are as shown in Table 3 below. It should be noted that with respect to the accuracy, values each obtained by subtracting an actually measured retention index from the corresponding estimated retention index, then dividing the obtained difference by the actually measured retention index, and multiplying the quotient by 100 are shown.

TABLE 3

| 8° C./min | Estimated retention index | Actually measured retention index | Accuracy % |
| --- | --- | --- | --- |
| 2-Octanone | 970.145 | 970.163 | 0.0018 |
| 1-Octanol | 1052.06 | 1052.44 | 0.036 |
| 2.6-Dimethylphenol | 1077.29 | 1077.21 | −0.0071 |
| 2.6-Dimethylaniline | 1131.87 | 1131.79 | −0.0076 |

As can be seen from Table 3, with respect to all of the samples, the retention indices were estimated with an accuracy within ±0.05%. Moreover, estimated retention times to be calculated based on these estimated retention indices can also be estimated with high accuracy.

As described above, with the gas chromatograph data processing device 100 according to the first embodiment, based on the HT-r relationship and the RI-HT relationship that were found by the inventor of the present invention, it is possible to estimate an estimated retention index and an estimated retention time with respect to any desired received rate of temperature increase such that the estimated values are very close to the actual values.

Moreover, with the estimation method according to the first embodiment, retention indices measured by isothermal analysis are no longer necessary, and a retention index with respect to any desired rate of temperature increase can be estimated based on retention indices measured by programmed-temperature analysis and rates of temperature increase used in the measurement of those retention indices. Accordingly, it is possible to effectively use data on retention indices obtained by programmed-temperature analysis, which is an analysis method that is actually commonly used.

Furthermore, since a retention index with respect to any desired rate of temperature increase can be estimated, in the case where, for example, a qualitative analysis of an unknown specimen is to be performed, it is no longer necessary to set the same rate of temperature increase as that of previously performed programmed-temperature analysis, and it is possible to freely set a rate of temperature increase that is suitable for the qualitative analysis.

Figure 5:
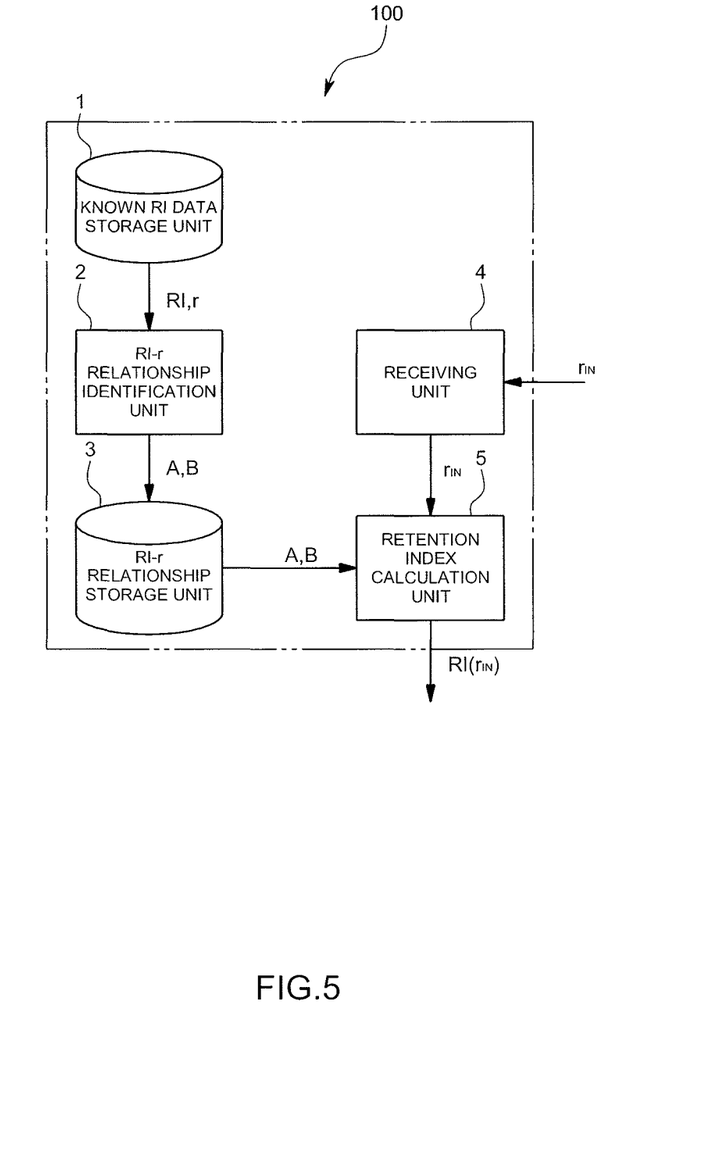
FIG. 5 shows a gas chromatograph data processing device according to a second embodiment of the present invention.

Next, the gas chromatograph data processing device 100 according to a second embodiment will be described. It should be noted that units that correspond to the various units described in the first embodiment are denoted by the same reference numerals.

The gas chromatograph data processing device 100 of the second embodiment is configured to identify the RI-r relationship using only the retention index and the rate of temperature increase instead of identifying the RI-r relationship by separately identifying the HT-r relationship and the RI-HT relationship, and is configured to calculate an estimated retention index corresponding to a received rate of temperature increase based on the identified RI-r relationship.

More specifically, as shown in FIG. 5, the gas chromatograph data processing device 100 of the second embodiment includes the known RI data storage unit 1, the RI-r relationship identification unit 2, the RI-r relationship storage unit 3, and the retention index calculation unit 5. Hereinafter, those portions that are different from the first embodiment will be described.

Figure 6:
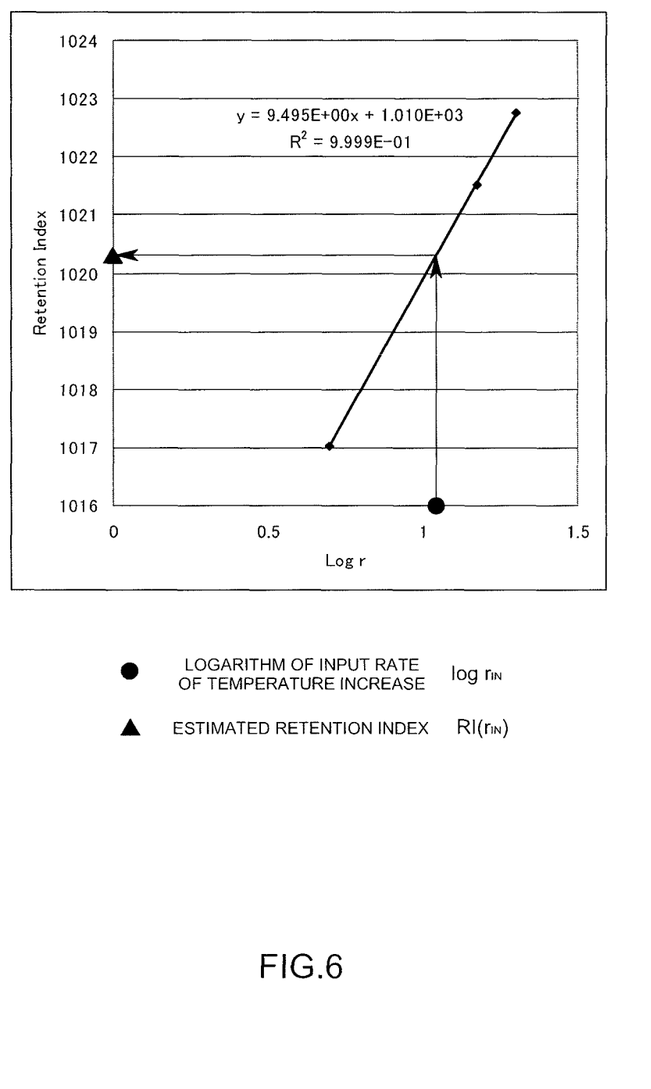
FIG. 6 is a schematic graph showing an RI-r relationship and a method for calculating an estimated retention index from a received rate of temperature increase according to the second embodiment.

The RI-r relationship identification unit 2 identifies the RI-r relationship based on a plurality of actually measured data items stored in the known RI data storage unit 1, that is, pairs of retention indices and rates of temperature increase used in the measurement of those retention indices. More specifically, the RI-r relationship identification unit 2 allows the RI-r relationship to be represented by a relation in which the retention index and the logarithm of the rate of temperature increase are variables as shown in FIG. 6, identifies an approximate equation of that relation, and stores coefficients A and B representing the approximate equation in the RI-r relationship storage unit 3.

The retention index calculation unit 5 calculates an estimated retention index corresponding to the received rate of temperature increase using the coefficients A and B of an approximate straight line indicating the RI-r relationship. For example, as shown in the graph of FIG. 6, an estimated retention index corresponding to a received rate of temperature increase on an approximate straight line indicating the RI-r relationship is calculated by the retention index calculation unit 5.

Based on the data regarding the known retention indices shown in Table 1, estimated retention indices of the respective samples corresponding to a received rate of temperature increase of 8° C./min were calculated using the chromatograph data processing device 100 of the second embodiment, and the calculation results are shown below.

Figure 7:
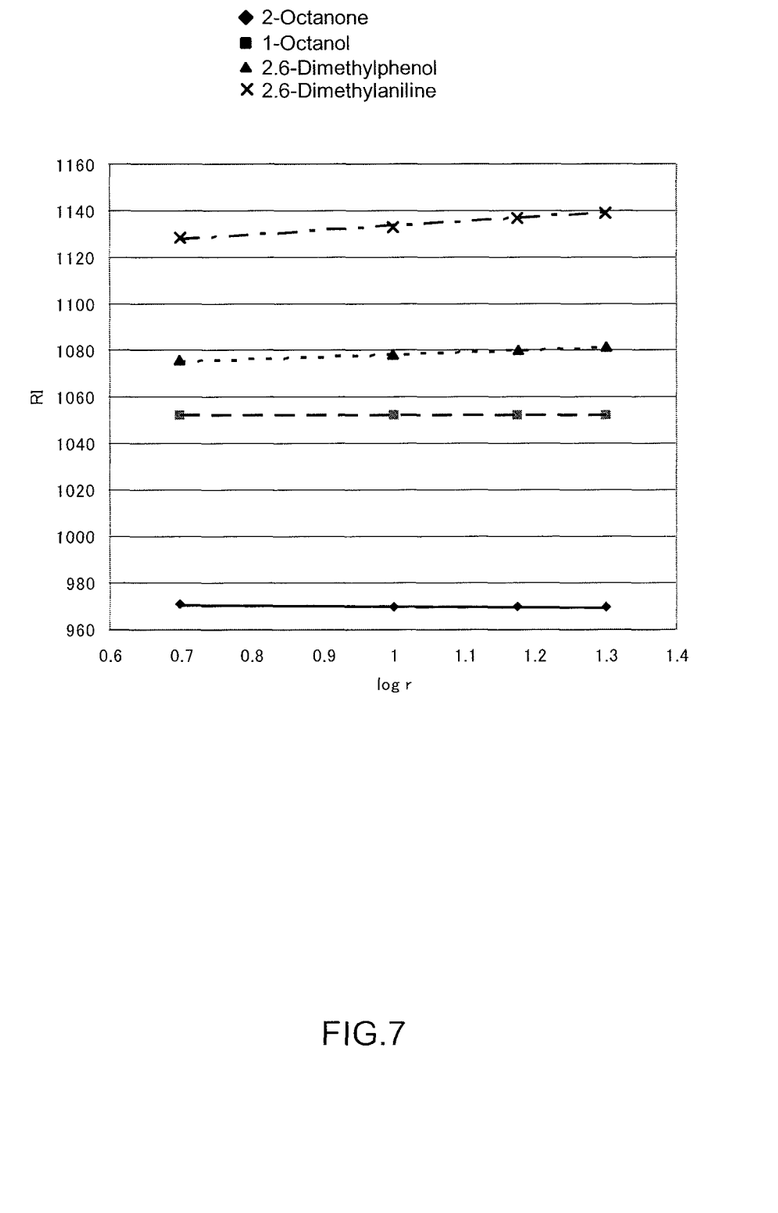
FIG. 7 is a graph showing the results of identification of relationships based on actually measured data according to the second embodiment.

Approximate straight lines indicating the RI-r relationships, which are the relationships between the retention index and the logarithm of the rate of temperature increase, of the respective samples that were identified by the RI-r relationship identification unit 2 are as shown in FIG. 7, and the slopes A and the intercepts B of the identified approximate straight lines individually take values shown in Table 4.

TABLE 4

| | RI-r relationship | | | |
| --- | --- | --- | --- | --- |
| | 2-Octanone | 1-Octanol | 2.6-Dimethylphenol | 2.6-Dimethylaniline |
| Slope A | −2.09394 | −0.451463 | 9.32509 | 18.6124 |
| Intercept B | 972.047 | 1052.47 | 1068.87 | 1115.06 |

Then, estimated retention indices corresponding to the received rate of temperature increase of 8° C./min were estimated using the values of A and B, and the estimation results are as shown in Table 5.

TABLE 5

| 8° C./min | Estimated retention index | Actually measured retention index | Accuracy % |
| --- | --- | --- | --- |
| 2-Octanone | 970.156 | 970.163 | 0.00065 |
| 1-Octanol | 1052.06 | 1052.44 | 0.036 |

TABLE 5-continued

| 8° C./min | Estimated retention index | Actually measured retention index | Accuracy % |
|---|---|---|---|
| 2.6-Dimethylphenol | 1077.29 | 1077.21 | −0.0072 |
| 2.6-Dimethylaniline | 1131.87 | 1131.79 | −0.0074 |

As can be seen from Table 5, the method for estimating a retention index according to the second embodiment also makes it possible to perform estimation with an accuracy substantially equal to that of the first embodiment. That is to say, the gas chromatograph data processing device 100 of the second embodiment can also have substantially the same effects as the first embodiment.

Other embodiments will be described.

In the foregoing embodiments, the inverses and the logarithms are obtained with respect to the retention temperature and the rate of temperature increase so that linearity appears in the RI-r relationship, the HT-r relationship, and the RI-HT relationship, and after the linearity appears, relations are identified. However, for example, a configuration may also be adopted in which the relations are identified as, for example, nonlinear functions such as quadratics, cubits, and the like. In such a case as well, there is a one-to-one correspondence between the retention index and the rate of temperature increase, and thus a retention index corresponding to any desired rate of temperature increase can be estimated.

Moreover, according to the foregoing embodiments, an estimated retention index corresponding to a received rate of temperature increase is calculated from retention indices measured by programmed-temperature analyses in which the temperature increase is started at the point in time when the sample is injected into the column. However, the estimation method according to the present invention can be used even with retention indices that are obtained by programmed-temperature analyses in which, for example, a constant temperature is maintained for a predetermined period of time from the injection of the sample into the column and the temperature increase is started after the lapse of this predetermined period of time. Furthermore, it is also possible to omit the known RI data storage unit and perform the estimation of a retention index by referring to a library such as the NIST via the Internet or the like and acquiring required retention indices obtained by programmed-temperature analysis.

In addition, an RI-r relationship storage unit in which RI-r relationships estimated by the method described in the foregoing embodiments are stored in advance may also be used as a database for use in the retention index estimation.

Furthermore, according to the foregoing embodiments, the gas chromatograph data processing device is configured such that all the calculations, storage processing, and the like are performed within a single device. However, the gas chromatograph data processing device may also be configured by a plurality of computers and the like. For example, the gas chromatograph data processing device may be configured in a divided manner in which the configuration of the database portion serving as the basis of the retention index estimation and the configuration for estimating, using the HT-r relationship and the RI-HT relationship identified from known data, a retention index, an adjusted retention time (adjusted retention time), or a retention time with respect to a rate of temperature increase at which no actual measurement has been performed are configured as separate devices.

Moreover, the present invention is not limited to data that is obtained by a gas chromatograph and may also be used for data that is obtained by a liquid chromatograph, and the present invention may also be configured as a liquid chromatograph data processing device.

In addition, various modifications and combinations of the embodiments may be made without departing from the gist of the present invention.

INDUSTRIAL APPLICABILITY

According to the present invention, it is possible to provide a chromatograph data processing device that can accurately estimate a retention index with respect to any desired rate of temperature increase if only a plurality of known retention indices and corresponding rates of temperature increase are known.

The invention claimed is:

1. A chromatograph data processing device comprising:
a processor; and
a memory that stores a program,
wherein, the program causes the processor to perform the following:
receiving a rate of temperature increase;
stores storing an RI-r relationship, the RI-r relationship being a relationship between a retention index and a rate of temperature increase and being identified based on a plurality of retention indices with respect to different rates of temperature increase and the corresponding rates of temperature increase; and
calculating an estimated retention index based on the RI-r relationship, the estimated retention index being a retention index corresponding to the received rate of temperature increase, thereby allowing a qualitative analysis of an unknown specimen.

2. The chromatograph data processing device according to claim 1, wherein the program further causes the processor to perform the following:
storing an HT-r relationship, the HT-r relationship being a relationship between a retention temperature and a rate of temperature increase and being identified based on a plurality of retention indices with respect to different rates of temperature increase and the corresponding rates of temperature increase; and
storing an RI-HT relationship, the RI-HT relationship being a relationship between a retention index and a retention temperature and being identified based on a plurality of retention indices with respect to different rates of temperature increase and the corresponding rates of temperature increase;
calculating an estimated retention temperature based on the HT-r relationship, the estimated retention temperature being a retention temperature corresponding to the received rate of temperature increase; and
calculating, based on the RI-HT relationship, a retention index corresponding to the estimated retention temperature as the estimated retention index.

3. The chromatograph data processing device according to claim 2,
wherein the HT-r relationship is represented by a relation in which an inverse of the retention temperature and a logarithm of the rate of temperature increase are variables.

4. The chromatograph data processing device according to claim 2, wherein the RI-HT relationship is represented by a relation in which the retention index and an inverse of the retention temperature are variables.

5. The chromatograph data processing device according to claim 2, wherein the program further causes the processor to perform the following:
   identifying the HT-r relationship based on a plurality of rates of temperature increase and retention temperatures corresponding to the respective rates of temperature increase; and
   identifying the RI-HT relationship based on a plurality of retention indices and retention temperatures corresponding to the respective retention indices;
   storing the identified HT-r relationship; and
   storing the identified RI-HT relationship.

6. The chromatograph data processing device according to claim 1,
   wherein the RI-r relationship is represented by a relation in which the retention index and a logarithm of the rate of temperature increase are variables.

7. The chromatograph data processing device according to claim 6, wherein the program further causes the processor to perform the following:
   identifying the RI-r relationship based on a plurality of retention indices and rates of temperature increase corresponding to the respective retention indices; and
   storing the identified RI-r relationship.

8. The chromatograph data processing device according to claim 1, wherein the program further causes the processor to perform the following:
   calculating an estimated retention time that is a retention time corresponding to the estimated retention index.

9. The chromatograph data processing device according to claim 1, further comprising a database that is configured to:
   store the RI-r relationship with respect to each of a plurality of substances, the RI-r relationship being the relationship between the retention index and the rate of temperature increase.

10. A chromatograph data processing method comprising:
    a receiving step of receiving a rate of temperature increase;
    an RI-r relationship storing step of storing an RI-r relationship, the RI-r relationship being a relationship between a retention index and a rate of temperature increase; and
    a retention index calculating step of calculating an estimated retention index based on the RI-r relationship, the estimated retention index being a retention index corresponding to a received rate of temperature increase that is the rate of temperature increase received in the receiving step, thereby allowing a qualitative analysis of an unknown specimen.

11. A non-transitory computer readable storage medium that stores a program for a chromatograph data processing device, the program causing a computer to perform the functions of:
    receiving a rate of temperature increase;
    storing an RI-r relationship, the RI-r relationship being a relationship between a retention index and a rate of temperature increase; and
    calculating an estimated retention index based on the RI-r relationship, the estimated retention index being a retention index corresponding to the received rate of temperature increase, thereby allowing a qualitative analysis of an unknown specimen.

* * * * *

UNITED STATES PATENT AND TRADEMARK OFFICE
CERTIFICATE OF CORRECTION

PATENT NO.        : 10,605,671 B2
APPLICATION NO.   : 14/894105
DATED             : March 31, 2020
INVENTOR(S)       : T. Maeda et al.

Page 1 of 1

It is certified that error appears in the above-identified patent and that said Letters Patent is hereby corrected as shown below:

At Column 14, Line 27 (Claim 1), please change "stores storing" to -- storing --

Signed and Sealed this
Eighth Day of September, 2020

Andrei Iancu
*Director of the United States Patent and Trademark Office*